United States Patent [19]

Eckstein et al.

[11] 4,317,782
[45] Mar. 2, 1982

[54] DISTYRYL COMPOUNDS

[75] Inventors: Udo Eckstein, Cologne; Edgar Siegel, Leverkusen, both of Fed. Rep. of Germany

[73] Assignee: Bayer Aktiengesellschaft, Leverkusen, Fed. Rep. of Germany

[21] Appl. No.: 13,894

[22] Filed: Feb. 22, 1979

[30] Foreign Application Priority Data

Feb. 22, 1978 [DE] Fed. Rep. of Germany ....... 2807497

[51] Int. Cl.$^3$ ................ C07C 9/40; C09K 11/02; C07F 9/53
[52] U.S. Cl. .................... 260/932; 260/940; 260/941; 260/947; 260/951; 260/505 C; 260/465 K; 542/412; 560/8; 560/14; 562/429; 562/465; 252/DIG. 17; 252/301.22; 252/301.21; 372/53
[58] Field of Search ............ 260/932, 956, 346.22, 260/940, 941, 947, 951, 465 K, 505 C; 542/412; 560/8, 14; 562/429, 465

[56] References Cited

U.S. PATENT DOCUMENTS 3,822,305 7/1974 Pintschovius et al. ............. 260/947

FOREIGN PATENT DOCUMENTS 2807497 8/1979 Fed. Rep. of Germany ...... 260/932

Primary Examiner—Anton H. Sutto
Attorney, Agent, or Firm—Sprung, Felfe, Horn, Lynch & Kramer

[57] ABSTRACT

Distyryl compounds of the formula

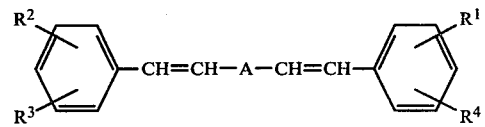

wherein
A denotes 1,4-phenylene, 4,4'-biphenylylene, 4,4''-terphenylylene, 1,4-, 1,5- or 2,6-naphthylene, 9,10-dihydro-2,7-phenanthrenylene or 2,7-dibenzofuranylene,
$R^1$ denotes an optionally functionally modified phosphonic acid, phosphonyl or phosphinyl group,
$R^2$ denotes hydrogen, an optionally functionally modified phosphonic acid, phosphonyl or phosphinyl group, sulpho, carboxyl, alkoxycarbonyl, aryloxycarbonyl, aralkoxycarbonyl, aminocarbonyl, cyano, halogen, alkyl, aralkyl, alkenyl, hydroxyl, alkoxy, aralkoxy, cycloalkoxy, aryloxy or alkylmercapto and
$R^3$ and $R^4$ denote hydrogen, halogen, alkyl, alkenyl, aryl, aralkyl, alkoxy, alkoxycarbonyl, aminocarbonyl, cyano, sulpho, aminosulphonyl, acyl, acylamino, hydroxyl, aryloxy, aralkoxy, alkenyloxy, carboxyl or acyloxy and wherein
the cyclic and acyclic radicals can contain non-chromophoric substituents, processes for the preparation of these compounds and their use for whitening synthetic, semi-synthetic and natural organic, high-molecular materials and for the production of laser radiation.

3 Claims, No Drawings

DISTYRYL COMPOUNDS

The invention relates to phosphono-, phosphonyl- and phosphinyl-substituted distyryl compounds, processes for their preparation and their use as whiteners and as laser dyestuffs.

The novel compounds correspond to the general formula

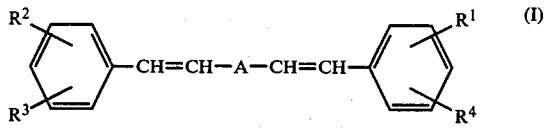

wherein

A denotes 1,4-phenylene, 4,4'-biphenylylene, 4,4''-terphenylylene, 1,4-, 1,5- or 2,6-naphthylene, 9,10-dihydro-2,7-phenanthrenylene or 2,7-dibenzofuranylene, $R^1$ denotes an optionally functionally modified phosphonic acid, phosphonyl or phosphinyl group, $R^2$ denotes hydrogen, an optionally functionally modified phosphonic acid, phosphonyl or phosphinyl group, sulpho, carboxyl, alkoxycarbonyl, aryloxycarbonyl, aralkoxycarbonyl, aminocarbonyl, cyano, halogen, alkyl, aralkyl, alkenyl, hydroxyl, alkoxy, aralkoxy, cycloalkoxy, aryloxy or alkylmercapto and $R^3$ and $R^4$ denote hydrogen, halogen, alkyl, alkenyl, aryl, aralkyl, alkoxy, aminocarbonyl, cyano, sulpho, aminosulphonyl, acyl, acylamino, hydroxyl, aryloxy, aralkoxy, alkenyloxy, carboxyl or acyloxy and wherein the cyclic and acyclic radicals can contain non-chromophoric substituents.

Non-chromophoric substituents are, for example, halogen, optionally substituted alkyl, optionally substituted alkenyl, aryl, aralkyl, optionally substituted alkoxy, alkoxycarbonyl, optionally substituted aminocarbonyl, cyano, sulpho, optionally substituted aminosulphonyl, acyl, acylamino, hydroxyl, aryloxy, aralkyloxy, alkenyloxy, carboxyl or acyloxy.

The phosphonic acid groups can be either in the form of the free acids or in the form of salts, in which case the water-soluble salts, such as the alkali metal salts and optionally substituted ammonium salts, are particularly preferred. Functionally modified phosphonic acid groups are to be understood as meaning preferentially the radicals

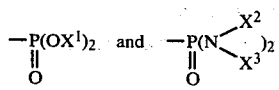

in which $X^1$ denotes alkyl, aralkyl, alkenyl or aryl, which are optionally further substituted, $X^2$ denotes hydrogen or alkyl, aralkyl, alkenyl or aryl which are optionally substituted by hydroxyl, halogen, alkoxy, cyano, carboxyl, carbalkoxy, sulpho, amino, monoalkylamino or dialkylamino, or together with $X_3$ and the nitrogen atom denotes optionally substituted morpholino, piperidino, piperazino, pyrrolidino or hexamethyleneimino and $X^3$ denotes hydrogen or alkyl which is optionally substituted by hydroxyl, halogen, alkoxy, cyano, carboxyl, carbalkoxy, sulpho, amino or mono- or dialkylamino, or together with $X_2$ and the nitrogen atom denotes optionally substituted morpholino, piperidino, piperazino, pyrrolidino or hexamethyleneimino.

Phosphonyl and phosphinyl groups are, in particular, radicals of the formula

wherein $Y^1$ denotes halogen or optionally substituted alkyl, aryl or aralkyl and $Y^2$ denotes halogen or optionally substituted alkyl, aryl or aralkyl, hydroxyl, alkoxy, aralkoxy, cycloalkoxy, aryloxy, amino, mono- or di-alkylamino, aralkylamino, acylamino, arylamino, cycloalkylamino, morpholino, piperidino or pyrrolidino.

Alkyl is in particular $C_1$–$C_4$-alkyl, which can be monosubstituted by hydroxyl, $C_1$–$C_4$-alkoxy, cyano, carboxyl, $C_1$–$C_4$-alkoxycarbonyl, aminocarbonyl, chlorine or bromine, or is trifluoromethyl.

Alkenyl is in particular $C_2$–$C_5$-alkenyl, which can be monosubstituted by hydroxyl, $C_1$–$C_4$-alkoxy, cyano, carboxyl, $C_1$–$C_4$-alkoxycarbonyl, chlorine or bromine. Vinyl and allyl are preferred.

Halogen is in particular fluorine, chlorine and bromine, preferably chlorine.

Aryl is in particular phenyl which is optionally substituted by $C_1$–$C_4$-alkyl, trifluoromethyl, chlorine, bromine, carboxyl, cyano, $C_1$–$C_4$-alkoxycarbonyl or $C_1$–$C_4$-alkoxy.

Aralkyl is in particular phenyl-$C_1$–$C_4$-alkyl, which can be further substituted in the phenyl nucleus by chlorine, methyl or methoxy.

Alkoxy is in particular $C_1$–$C_4$-alkoxy or a radical of the formula

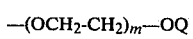

in which

Q denotes hydrogen or $C_1$–$C_4$-alkyl and m denotes an integer from 1 to 20.

Cycloalkyloxy and cycloalkylamino are, in particular, cyclopentyloxy, cyclopentylamino, cyclohexyloxy and cyclohexylamino.

Acyl is in particular $C_1$–$C_4$-alkylcarbonyl, $C_1$–$C_4$-alkoxycarbonyl, $C_1$–$C_4$-alkylsulphonyl, $C_1$–$C_4$-alkoxysulphonyl, benzoyl which is optionally substituted by methyl, methoxy or chlorine, benzenesulphonyl which is optionally substituted by methyl, methoxy or chlorine, phenyl-$C_1$–$C_4$-alkoxycarbonyl which is optionally substituted by methyl, methoxy or chlorine, or phenoxycarbonyl which is optionally substituted by methyl, methoxy or chlorine.

Possible substituents of the aminocarbonyl and aminosulphonyl radicals are, in particular, $C_1$–$C_4$-alkyl, phenyl which is optionally substituted by methyl, methoxy or chlorine, or phenyl-$C_1$–$C_4$-alkyl.

Preferred compounds correspond to the formula

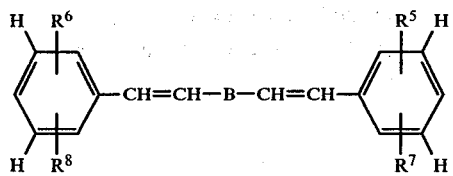 (II)

wherein

B denotes 1,4-phenylene, 4,4'-biphenylylene, 1,4- and 2,6-naphthylene, 9,10-dihydro-2,7-phenanthrenylene or 2,7-dibenzofuranylene, $R^5$ denotes a radical of the formula

$R^6$ denotes hydrogen, chlorine, $C_1$–$C_4$-alkyl, sulpho, carboxyl, $C_1$–$C_4$-alkoxy, $C_1$–$C_4$-alkoxycarbonyl, cyano or a radical of the formula

$R^7$ and $R^8$ denote hydrogen, chlorine, $C_1$–$C_4$-alkyl, phenyl which is optionally substituted by methyl, methoxy or chlorine, $C_1$–$C_4$-alkoxy, $C_1$–$C_4$-alkoxycarbonyl, cyano, $C_1$–$C_4$-alkylsulphonyl, $C_1$–$C_4$-alkylcarbonyl, hydroxyl or carboxyl, $R^9$ and $R^{10}$ denote $C_1$–$C_4$-alkyl, benzyl, phenyl which is optionally substituted by methyl, methoxy or chlorine, a group of the formulae —OH or —$OR^{11}$ or a radical of the formula

—(OCH$_2$CH$_2$)$_n$-OR$^{11}$ $R^{11}$ denotes hydrogen, $C_1$–$C_4$-alkyl, benzyl or phenyl and n denotes an integer from 1 to 7, it being possible for the phosphonic or phosphinic acid groups also to be in the form of salts.

Particularly valuable compounds correspond to the formula

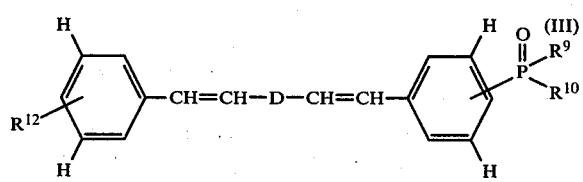 (III)

wherein

D denotes 1,4-phenylene, 4,4'-biphenylylene or 9,10-dihydro-2,7-phenanthrenylene and $R^{12}$ denotes hydrogen, chlorine, $C_1$–$C_4$-alkyl, phenyl, $C_1$–$C_4$-alkoxy, $C_1$–$C_4$-alkoxycarbonyl, cyano, $C_1$–$C_4$-alkylcarbonyl, hydroxyl or carboxyl or a radical of the formula

in which $R^9$ and $R^{10}$ have the abovementioned meaning.

The distyryl compounds of the formula (I) can be prepared by methods which are in themselves known, by reacting the compound of the formula $$Z^1—A—Z^2 \quad (IV)$$

in a molar ratio of 1:1:1 with one compound of the formula

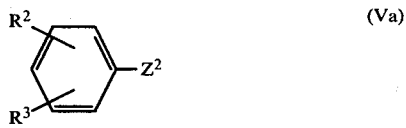 (Va)

and one compound of the formula

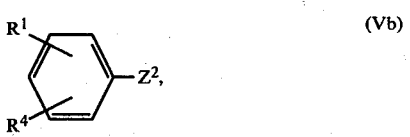 (Vb)

in which formulae one of each of the symbols $Z_1$ and $Z_2$ represents a formyl group and the other represents a grouping of the formula

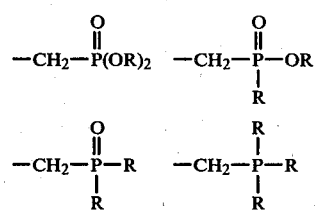

wherein

R denotes a $C_1$–$C_4$-alkyl, a $C_5$–$C_6$-cycloalkyl or an aryl radical which is optionally further substituted, preferably a phenyl radical.

Symmetrical and asymmetrical compounds and mixtures of symmetrical and asymmetrical compounds can be prepared in this way.

Accordingly, for example, dialdehydes of the formula $$O{=}CH—A—CH{=}O \quad (VI)$$

can be reacted with monofunctional compounds of the formulae

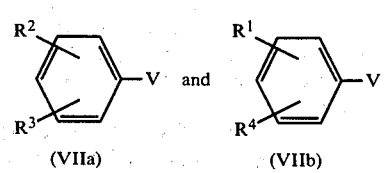
(VIIa)　　　　(VIIb)

or monoaldehydes of the formulae $$\underset{\text{(VIIIa)}}{\overset{R^2}{\underset{R^3}{\bigotimes}}-CH=O} \quad \text{and} \quad \underset{\text{(VIIIb)}}{\overset{R^1}{\underset{R^4}{\bigotimes}}-CH=O}$$

can be reacted with bifunctional compounds of the formula $$V-A-V \quad \quad (IX)$$

in which formulae

A, $R^1$, $R^2$, $R^3$ and $R^4$ have the indicated meaning and V denotes $$-CH_2-\overset{O}{\underset{}{\overset{\|}{P}}}-(OR)_2, \quad -CH_2-\overset{O}{\underset{R}{\overset{\|}{P}}}-OR,$$

$$-CH_2-\overset{O}{\overset{\|}{P}}-(R)_2 \text{ or } -CH_2-P(R)_3.$$

The phosphorus compounds of the formulae (VIIa), (VIIb) and (IX) required as starting materials for this process are obtained by reacting halogenomethyl compounds, preferably chloromethyl or bromomethyl compounds, of the formulae $$\underset{\text{(Xa)}}{\overset{R^2}{\underset{R^3}{\bigotimes}}-CH_2-Hal} \quad \text{or}$$

$$\underset{\text{(Xb)}}{\overset{R^1}{\underset{R^4}{\bigotimes}}-CH_2-Hal} \quad \text{and}$$

$$Hal-CH_2-A-CH_2-Hal \quad \quad (XI)$$

with phosphorus compounds $P(OR)_3$, $R-P(OR)_2$, $RO-P(R)_2$ or $P(R)_3$, in which R has the indicated meaning. Preferably, R denotes $C_1-C_4$-alkyl when bonded to oxygen but phenyl when bonded to phosphorus.

In order to prepare the end products, the corresponding components are subjected to a condensation reaction in the presence of basic condensing agents in organic solvents.

The solvents chosen are advantageously inert solvents, for example hydrocarbons, such as toluene or xylene, or alcohols, such as methanol, ethanol, isopropanol, butanol or glycol, glycol ethers, such as 2-methoxyethanol, hexanol, cyclohexanol, cyclooctanol and also ethers, such as diisopropyl ether, dioxane or tetrahydrofurane; furthermore formamides, N-methylpyrrolidone, dimethylsulphoxide and phosphoric acid amides, Dimethylformamide, dimethylacetamide and phosphoric acid tris-dialkylamides, in which alkyl is in particular $C_1-C_4$-alkyl, are preferred.

Condensing agents which can be used are strongly basic compounds, such as alkali metal hydroxides or alkaline earth metal hydroxides, alkali metal amides or alkaline earth metal amides and alkali metal alcoholates or alkaline earth metal alcoholates, for example potassium hydroxide, sodium hydroxide, potassium tert.-butylate, sodium amide or sodium methylate, and also the alkali metal compounds of dimethylsulphoxide and alkali metal hydrides, as well as, in some cases, alkali metal dispersions.

The reaction is preferably carried out in the temperature range of 0° to 120° C.

A further process for the preparation of compounds of the formula (I) comprises reacting the bis-halogeno compounds of the formula (XII)

$$\underset{Hal}{\overset{R^3}{\underset{}{\bigotimes}}}-CH=CH-A-CH=CH-\underset{Hal}{\overset{R^4}{\underset{}{\bigotimes}}} \quad (XII)$$

with phosphorus compounds of the formula $$RO-P\overset{R^9}{\underset{R^{10}}{\diagdown}} \quad \quad (XIII)$$

in which formulae

A, R, $R^3$, $R^4$, $R^9$ and $R^{10}$ have the indicated meaning and

Hal preferably denotes chlorine or bromine.

The condensation reaction can be carried out in the absence or in the presence of an organic solvent. The reaction without a solvent is preferred.

Suitable catalysts for the condensation reaction are heavy metal salts, which appropriately are added in amounts of 0.01 to 0.05 mol. Divalent and monovalent halides of the sub-group metals, such as CuCl, CuI, $CoCl_2$ and $NiCl_2$, are preferably used.

The reaction temperatures can be varied within a relatively wide range and in general the reaction is carried out at between 150° and 250° C., preferably at between 160° and 200° C.

The compounds of the formula (XII) are accessible by known processes.

The compounds (I) according to the invention are also obtained when the corresponding aldehyde-anils are reacted in a dipolar aprotic solvent such as dimethylformamide in the presence of basic condensing agents with the corresponding methyl compounds.

Yet further modifications which are in themselves known, such as halogenations, functional modifications of carboxyl groups, the introduction of chloromethyl groups or the replacement of halogen atoms by cyano groups, can also be carried out on the reaction products of the above processes.

In solution or in the finely divided state, the compounds of the formula (I) display a very strong blue fluorescence. They are suitable on their own or as mixtures for whitening very diverse synthetic, semi-synthetic or natural organic materials.

The new compounds of the formula I containing phosphonic acid ester groups are particularly suitable for whitening synthetic organic fibre materials based on polyesters or on plastics such as soft PVC, polyethylene and polypropylene. Latices of acrylic esters, polyvinyl esters and polystyrenes can also be brightened well.

On the other hand, the compounds of the formula (I), which contain phosphonic acid groups are suitable for whitening cotton, cellulose and polyamides from wash liquors. Compared with comparable compounds, they have advantages in respect of whiteness, the fastness to light and the solubility in water.

With their high quantum yield and high fastness to light, compounds of the formula (I) can also be used as variable dyestuff lasers in the blue spectral region from 400 nm–480 nm. For this purpose, they are used in the arrangement described in DE-OS (German Published Specification) No. 1,764,982 and DE-OS (German Published Specification) No. 1,910,784.

The following groups of organic materials, insofar as these can undergo optical brightening, may be mentioned as examples for the diverse use of the compounds as brighteners, without any restriction being implied by the following classification:

I.

Synthetic organic high-molecular materials:

(a) Polymerisation products based on organic compounds containing at least one polymerisable carbon-carbon double bond, that is to say the homopolymers or copolymers thereof and also the after-treatment products thereof, such as, for example, crosslinking, grafting or degradation products, polymer blends and the like, and examples of these products which may be mentioned are: polymers based on $\alpha,\beta$-unsaturated carboxylic acids, especially on acrylic compounds (such as, for example, acrylates, acrylic acids, acrylonitrile and acrylamides and their derivatives or their methacrylic analogues) or on olefine hydrocarbons (such as, for example, ethylene, propylene, isobutylene, styrenes and dienes such as, in particular, butadiene or isoprene, that is to say thus also including rubbers and rubber-like polymers, and also so-called ABS polymers), polymers based on vinyl and vinylidene compounds (such as, for example, vinyl esters, vinyl chloride, vinylsulphonic acid, vinyl ethers, vinyl alcohol, vinylidene chloride or vinylcarbazole), on halogenated hydrocarbons (chloroprene or subsequently halogenated ethylenes), on unsaturated aldehydes and ketones (for example acrolein and the like) and on allyl compounds and the like, graft polymerisation products (for example by grafting on vinyl monomers), crosslinking products (for example by means of bifunctional or polyfunctional cross-linking agents such as divinylbenzene, polyfunctional allyl compounds or bis-acrylic compounds) or . . . are obtainable by partial degradation (hydrolysis or depolymerisation) or modification of reactive groupings (for example esterification, etherification, halogenation and spontaneous cross-linking).

(b) Other polymerisation products such as are obtainable, for example, by ring opening, for example polyamides of the polycaprolactam type, and also formaldehyde polymers or polymers which are obtainable either via polyaddition or via polycondensation, such as polyethers, polythioethers, polyacetals and thioplasts.

(c) Polycondensation products or precondensates based on bi- or poly-functional compounds with condensable groups, the homocondensation and cocondensation products thereof and also after-treatment products; examples of these products which may be mentioned are: polyesters, which are saturated (for example polyethylene terephthalate) or unsaturated (for example maleic acid/dialcohol polycondensates and also their crosslinking products with copolymerisable vinyl monomers), non-branched or branched (including those based on polyhydric alcohols, such as, for example, alkyd resins); polyamides (for example hexamethylenediamine adipate), maleate resins, melamine resins, phenol resins, aniline resins, furane resins and carbamide resins and also their precondensates and products of analogous structure, polycarbonates, silicone resins and others.

(d) Polyaddition products, such as polyurethanes (crosslinked and non-crosslinked) and epoxide resins.

II.

Semi-synthetic organic materials, such as, for example, cellulose esters and mixed esters (acetate or propionate), nitrocellulose, cellulose ethers, regenerated cellulose (viscose or cuprammonium cellulose) or the after-treatment products thereof and casein plastics.

III.

Natural organic materials of animal or vegetable origin, for example based on cellulose or proteins, such as wool, cotton, silk, bast, jute, hemp, skins and hairs, leather, wood compositions in fine division, natural resins (such as colophony and especially varnish resins) and also rubber, gutta percha and balata and also their after-treatment and modification products, (for example obtained by curing, cross-linking or grafting), degradation products (for example obtained by hydrolysis or depolymerisation) and products obtainable by the modification of reactive groups (for example by acylation, halogenation, crosslinking and the like).

The organic materials which can be used can be in the most diverse states of processing (raw materials, semi-finished goods or finished goods) and aggregate states. On the one hand, they can be in the form of structures of the most diverse shapes, that is to say, for example, predominantly three-dimensionally expanded structures, such as blocks, sheets, profiles, tubes, injection mouldings or very diverse machined articles, chips or granules or foams; predominantly two-dimensional structures, such as films, foils, lacquers, tapes, coverings, impregnations and coatings, or predominantly one-dimensional bodies, such as filaments, fibres, flocks, bristles and wires. The said materials can, on the other hand, also be in an unshaped state, in the most diverse homogeneous or inhomogeneous forms of division and aggregate states, for example in the form of powders, solutions, emulsions, dispersions or latices (examples: lacquer solutions, polymer dispersions, sols, jelly, putties, pastes, waxes, adhesive compositions and trowelling compounds and the like).

Fibre materials can be, for example, in the form of continuous filaments, staple fibres, flocks, hanks, textile filaments, yarns, threads, non-wovens, felts, waddings or flock structures or in the form of woven textile or bonded textile fabrics or knitted fabrics or also in the form of paper, cardboards or paper pulps and the like.

The compounds to be used according to the invention are also of importance for the treatment of organic textile materials, especially woven textile fabrics. If fibres which can be in the form of staple fibres or continuous filaments or in the form of hanks, woven fabrics, knitted fabrics, fleeces, flocked substrates or bonded fabrics are to be whitened according to the invention, this is advantageously effected in an aqueous medium in which the compounds in question are present in a finely divided form (a suspension or optionally a solution). If desired, dispersing agents, such as, for example, soaps, polyglycol ethers of fatty alcohols, fatty amines or alkylphenols, cellulose sulphite waste liquor or condensation products of optionally alkylated naphthalenesulphonic acids with formaldehyde, can be added during the treatment. It proves particularly appropriate to carry out the treatment in a neutral, weakly alkaline or acid bath. It is also advantageous if the treatment is carried out at elevated temperatures of about 50° to 100° C., for example at the boiling point of the bath or near it (about 90° C.). Solutions in organic solvents can also be used for the finishing according to the invention, as is practised in the dyeing industry in so-called solvent dyeing (pad-thermofixation, or exhaust dyeing processes in drum dyeing machines), for example of polyamide and polyester substrates.

The new whiteners to be used according to the invention can furthermore be added to, or incorporated in, the materials before or during their shaping. Thus, for example, they can be added to the compression moulding composition or injection moulding composition during the production of films, sheets, tapes or mouldings, or can be dissolved or dispersed in the spinning melt prior to spinning, or provision can be made in some other way to ensure a state of homogeneous fine division. The whiteners can also be added to the starting substances, reaction mixtures or intermediate products for the production of fully synthetic or semi-synthetic organic materials, that is to say including before or during the chemical reaction, for example in the case of a polycondensation (that is to say including precondensates) or in the case of a polymerisation (that is to say including prepolymers) or a polyaddition.

The new whiteners can, of course, also be employed wherever organic materials of the type indicated above are combined with inorganic materials in any form (typical examples: detergents and white pigments in organic substances).

The new whitening substances are distinguished by particularly good stability to heat, fastness to light and stability to migration.

The amount of the new whiteners to be used according to the invention, based on the material to be whitened, can vary within wide limits. A distinct and lasting effect can already be achieved with very small amounts, in certain cases, for example, amounts of 0.001% by weight. However, amounts of up to about 0.5% by weight and more can also be used. For most practical purposes, amounts of interest are preferably between 0.01 and 0.2% by weight.

The new compounds, which act as whiteners, can, for example, also be employed as follows:

(a) In mixtures with dyestuffs or pigments or as an additive to dyebaths, printing pastes, discharge pastes or reserve pastes. In addition, also for the after-treatment of dyeings, prints or discharge prints.

(b) In mixtures with so-called "carriers", antioxidants, light stabilisers, heat stabilisers and chemical bleaching agents or as an additive to bleaching baths.

(c) In a mixture with crosslinking agents or finishing agents, such as starch or finishes which are accessible synthetically. The products according to the invention can also advantageously be added to liquors used to obtain a crease-resistant finish.

(d) In combination with detergents. The detergents and brighteners can be added separately to the wash baths to be used. It is also advantageous to use detergents which contain the whiteners in admixture. Suitable detergents are, for example, soaps, salts of sulphonate detergents, such as, for example, of sulphonated benzimidazoles substituted on the carbon atom in the 2-position by higher alkyl radicals, and also salts of monocarboxylic acid esters of 4-sulphophthalic acid with higher fatty alcohols, and furthermore salts of fatty alcohol sulphonates, alkylarylsulphonic acids or condensation products of higher fatty acids with aliphatic hydroxy- or amino-sulphonic acids. Furthermore, nonionic detergents can be used, for example polyglycol ethers, which are derived from ethylene oxide and higher fatty alcohols, alkylphenols or fatty amines.

(e) In combination with polymeric carrier materials (polymerisation, polycondensation or polyaddition products), in which the whiteners are incorporated, optionally alongside other substances, in the dissolved or dispersed form, for example in coating or impregnating agents or binders (solutions, dispersions or emulsions), textiles, fleeces, paper or leather.

(f) As additives to a wide variety of industrial products in order to render these more marketable or to avoid disadvantages in their usefulness, for example as an additive to sizes, adhesives, toothpastes, paints and the like.

(g) In combination with other substances having a whitening action (for example in order to change the shade).

(h) In spinning bath preparations, that is to say as additives to spinning baths such as are used for improving the slip for the further processing of synthetic fibres.

The compounds of the formula indicated initially can also be used as scintillators for various purposes of a photographic nature, such as for electrophotographic reproduction or for supersensitising.

If the whitening process is combined with other treatment or finishing methods, the combined treatment is advantageously carried out with the aid of appropriate stable preparations. Such preparations are characterised in that they contain whitening compounds of the general formula indicated initially and also dispersing agents, detergents, carriers, dyestuffs, pigments or finishing agents.

When treating a number of fibre substrates, for example polyester fibres, with the whiteners according to the invention, the procedure followed is appropriately to impregnate these fibres with the aqueous dispersions of the whiteners at temperatures below 75° C., for example at room temperature, and to subject them to a dry heat treatment at temperatures above 100° C., it being generally advisable additionally to dry the fibre material beforehand at a moderately elevated temperature, for example at not below 60° C. to about 100° C. The heat treatment in the dry state is then advantageously carried out at temperatures between 120° and 225° C., for example by warming in a drying chamber, by ironing within the specified temperature range or by treatment with dry, superheated steam. The drying and dry heat treatment can also be carried out in immediate succession or combined in a single operation.

EXAMPLE 1

100 ml of a 1 molar solution of sodium ethylate in ethanol are added dropwise in the course of 30 minutes to a solution of 36.4 g (0.1 mol) of diethyl 4-diethoxyphosphonomethylbenzenephosphonate and 10.5 g (0.05 mol) of 4,4'-diformylbiphenyl in 50 ml of hexamethylphosphoric acid triamide at a rate such that the temperature does not rise above 50° C. The mixture is stirred for 4 hours at 40° to 50° C., the pH is adjusted to 4 to 5 with acetic acid, the bulk of the solvents is distilled off in vacuo and the residue is added to 200 ml of ice-water. The yellowish precipitate is filtered off, washed with water and dried. This gives 22.9 g (72.7% of theory) of a crude product of the formula

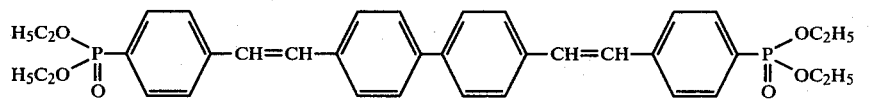

which is purified by repeated recrystallisation from xylene. When dissolved in dimethylformamide, the substance has a strong blue fluorescence and when incorporated in polyethylene terephthalate effects a strong white effect with good fastness properties.

The diethoxyphosphonomethyl compound of the formula

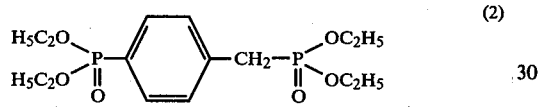

which is used is prepared in the following manner:

A mixture of 196 g (1.1 mols) of N-bromosuccinimide, 1.33 g of dibenzoyl peroxide and 1.33 g of azo-bis-isobutyronitrile is added in portions at 60° C. to a solution of 228 g (1 mol) of diethyl 4-methylbenzenephosphonate in 1,000 ml of anhydrous carbon tetrachloride and the mixture is stirred at the reflux temperature for a further 4 hours. Succinimide is then filtered off, the filter cake is washed with 100 ml of carbon tetrachloride and the filtrate is evaporated in vacuo. The oily crude product is sufficiently pure and is further processed without distillation (yield 90% of theory).

61.4 g (0.2 mol) of crude diethyl 4-bromomethylbenzenephosphonate are added dropwise at 150° C. to 49.8 g (0.3 mol) of triethyl phosphite. The temperature is then slowly raised to 180° C. in the course of 3 hours and the mixture is distilled under a high vacuum. This gives 60 g (82% of theory) with a boiling point at 0.5 mm Hg of 135° to 150° C.

The corresponding meta- and ortho-phosphono derivatives of the formula (2) are also obtained in the same way.

EXAMPLE 2

Analogously to Example 1, the reaction of diethyl 4-diethoxyphosphonomethylbenzenephosphonate with terephthalaldehyde gives 18.3 g (66% of theory) of the compound of the formula

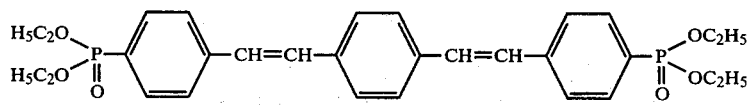

in the form of yellow crystals. These can be purified by recrystallisation from toluene/ligroin with the addition of bleaching earth; fluorescence in dimethylformamide: reddish-tinged blue.

EXAMPLE 3

In the same way as in Example 1, the compound of the formula

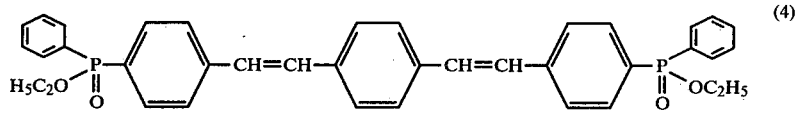

is obtained in the form of pale yellow crystals (toluene) from 39.6 g (0.1 mol) of ethyl (4-diethoxyphosphonomethylbenzene)-phenylphosphinate and 6.7 g (0.05 mol) of terephthalaldehyde: a solution of this product in dimethylformamide displays intense, reddish-tinged blue fluorescence.

EXAMPLE 4

51.6 g (0.1 mol) of 4,4'-di-(2-bromostyryl)biphenyl are added at 160° C. to a suspension of 0.6 g of nickel-II chloride and 33.2 g (0.2 mol) of triethyl phosphite at a rate such that the ethyl bromide distils off at a uniform rate and can be collected. In order to bring the reaction to completion, the reaction mixture is heated for about a further 2 to 3 hours at 200° C. The excess triethyl phosphite is then distilled off, the reaction mixture is allowed to cool to 100° C., 50 ml of toluene are added and the mixture is clarified with bleaching earth and filtered. 30 ml of methylcyclohexane are added to the filtrate and the substance is allowed to crystallise out. Yield: 41 g (65% of theory) of pale yellow crystals of the compound of the formula

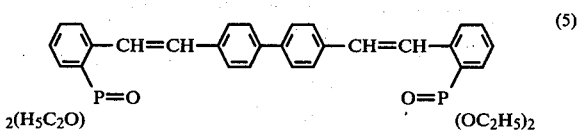

a solution of which in dimethylformamide displays an intense reddish-tinged blue fluorescence.

EXAMPLE 5

12.6 g (0.02 mol) of the compound (5) are heated under reflux with 4.5 g (0.08 mol) of potassium hydroxide in 50 ml of methylglycol for 10 hours. The solvent is then distilled off and the residue is dissolved in 100 ml of distilled water and the solution is clarified hot with active charcoal and filtered. The pH of the filtrate is then adjusted to 2 with concentrated hydrochloric acid. After filtering off and drying, 9.9 g (86.1% of theory) of pale yellow crystals of a compound having the structure

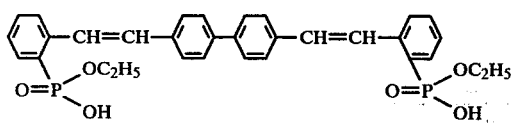

are obtained and, when recrystallised from dimethylformamide, these display a strong reddish-tinged blue fluorescence.

On the other hand, the compound of the formula

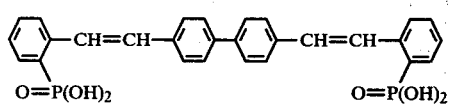

which when recrystallised from glacial acetic acid displays a reddish-tinged blue fluorescence, is obtained in an analogous manner from the same starting compounds by reaction above 150° C. in an autoclave.

EXAMPLE 6

In a similar manner, the compound of the structure

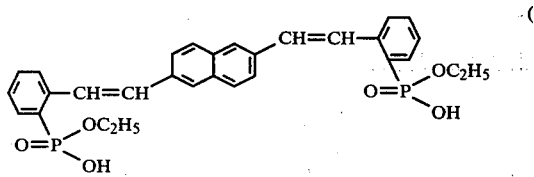

is obtained in the form of pale yellow crystals from 2,6-di-(2-bromostyryl)-naphthalene by reaction with triethyl phosphite and potassium hydroxide; these crystals are recrystallised from dimethylformamide and in this solvent display a strongly blue fluorescence.

EXAMPLE 7

30.7 g (0.1 mol) of diethyl 4-bromomethylbenzenephosphonate and 23.7 g (0.14 mol) of triethyl phosphite are stirred at the reflux temperature for 2 hours. The excess triethyl phosphite is then distilled off in vacuo and 100 ml of anhydrous dimethylformamide are added to the residue. 18.7 g (0.08 mol) of 4-formyl-4'-cyanostilbene are added to this solution and a solution of 2.3 g of sodium in 50 ml of ethanol is added dropwise at 50° C. in the course of 30 minutes. After the solution has been stirred under nitrogen for 4 hours at 50° C., the reaction mixture is discharged into 500 ml of water and the pH is adjusted to 4-5 with acetic acid. The mixture is extracted with three times 100 ml of chloroform. The organic phase is then washed once with 100 ml of saturated sodium carbonate solution and once with 100 ml of water. After drying over anhydrous sodium sulphate and filtering, the solvent is removed in vacuo. 50 ml of carbon tetrachloride are added to the residue. This gives 18.8 g (53% of theory) of a pale yellow crystalline powder of the compound of the formula

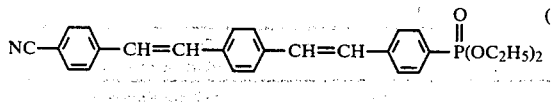

which is purified by recrystallisation from toluene. When dissolved in dimethylformamide, the substance displays a strongly blue fluorescence and when applied to polyester by the exhaustion process gives very good white effects with very good fastness properties.

In order to prepare the compound (9), it is also possible, with equal success, to use terephthalaldehyde and successively to carry out the reactions with the corresponding amounts of 2-diethoxyphosphonomethylbenzonitrile and diethyl 4-diethoxyphosphonomethylbenzenephosphonate. In place of dimethylformamide, hexamethylphosphoric acid triamide can also be used as the solvent. The asymmetrical compound of the formula (9) can be isolated from the mixture by recrystallisation or by separation by column chromatography.

EXAMPLE 8

In the same way as in Example 7, the compound of the formula

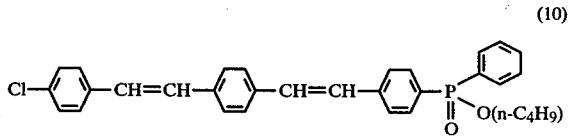

is obtained from 13.2 g (0.05 mol) of 4-diethoxyphosphonomethylchlorobenzene, 21.2 g (0.05 mol) of n-butyl (4-diethoxyphosphonomethylbenzene)-phenylphosphinate and 3.35 g (0.025 mol) of terephthalaldehyde. Pale yellow crystals are obtained from xylene and a solution of these crystals in dimethylformamide displays an intense, reddish-tinged blue fluorescence.

EXAMPLE 9

Analogously to Example 4, the compound of the formula

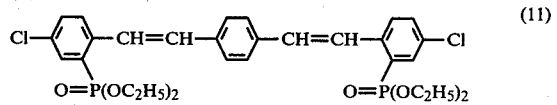

is obtained in the form of yellow crystals from the corresponding dibromodistyryl compounds and triethyl phosphite and these crystals are recrystallised from xylene and in dimethylformamide display a reddish-tinged blue fluorescence.

Further particularly valuable compounds which correspond to the formula

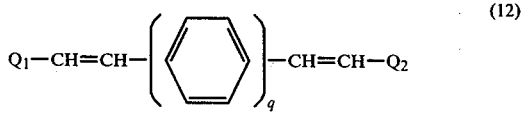

are listed in Table I which follows. The isolation of the asymmetrical compounds from the mixtures with the symmetrical compounds can be effected where appropriate on the basis of the differing solubilities of the compounds, by recrystallisation or by separation by column chromatography.

TABLE I $$Q_1-CH=CH-\left(\phantom{\bigg|}\!\!\!\!\bigcirc\!\!\!\!\phantom{\bigg|}\right)_q-CH=CH-Q_2$$

| No. | $Q_1$ | $Q_2$ | q | Fluorescence in DMF |
|---|---|---|---|---|
| 13 | 4-diethoxyphosphonophenyl | 2-cyanophenyl | 2 | neutral blue |
| 14 | 4-di-n-butoxyphosphonophenyl | 4-biphenylyl | 1 | blue |
| 15 | 4-diethoxyphosphonophenyl | 2-cyano-4-methoxyphenyl | 1 | blue |
| 16 | 4-diethoxyphosphonophenyl | 3-cyanophenyl | 2 | blue |
| 17 | 4-phosphonophenyl | 4-phosphonophenyl | 2 | reddish-tinged blue |
| 18 | 4-(hydroxy-phenyl-phosphonyl)-phenyl | 4-(hydroxy-phenyl-phosphonyl)-phenyl | 1 | intense blue |
| 19 | 2-carboxyphenyl | 2-phosphonophenyl | 2 | reddish-tinged blue |
| 20 | 3-phosphonophenyl | 2,4-disulphophenyl | 2 | strong light blue |
| 21 | 4-ethoxycarbonylphenyl | 4-diethoxyphosphonophenyl | 2 | blue-violet |
| 22 | 3-methoxy-4-methylphenyl | 4-diphenylphosphinylphenyl | 1 | greenish-tinged blue |
| 23 | 4-acetylphenyl | 4-(propyl-methoxyethoxy-phosphonyl)-phenyl | 2 | neutral blue |
| 24 | 4-(p-anisyl-ethoxy-phosphonyl)-phenyl | 2-phosphonophenyl | 2 | blue |
| 25 | 4-dibenzyloxyphosphono-phenyl | 4-dibenzyloxyphosphono-phenyl | 1 | red-violet |
| 26 | 3-choro-4-cyanophenyl | 4-diphenoxyphosphono-phenyl | 1 | blue |
| 27 | 2-methyl-4-cyanophenyl | 3-di-isopropoxyphosphono-phenyl | 1 | blue |
| 28 | 2-cyano-5-methoxyphenyl | 4-p-anisylmethoxyphos-phonylphenyl | 1 | greenish-tinged blue |
| 29 | 3-chloro-4-cyanophenyl | 3-chloro-4-diethoxy-phosphonophenyl | 2 | blue |
| 30 | 3-di-(2-methoxyethoxy)-phosphonophenyl | 3-di-(2-methoxyethoxy)-phosphonophenyl | 2 | blue |
| 31 | 2-phosphonophenyl | 2-phosphonophenyl | 2 | reddish-tinged blue |

EXAMPLE 10

13.6 g (0.2 mol) of sodium ethylate are added in portions in the course of 30 minutes to a solution of 23.4 g (0.05 mol) of 2,7-bis-(diethoxyphosphonomethyl)-dibenzofurane and 24.2 g (0.1 mol) of diethyl 4-formyl-benzenephosphonate in 150 ml of dimethylformamide. The reaction mixture is then stirred for 5 hours at 50° C. and discharged into 500 ml of water and the resulting mixture is neutralised with concentrated hydrochloric acid. After filtering off and drying, 23.5 g (73% of theory) of the compound of the formula

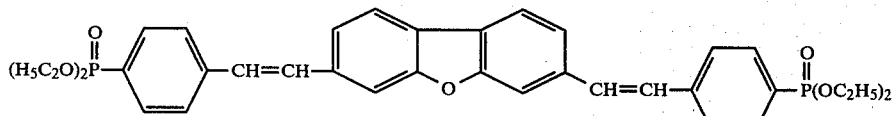

are obtained in the form of a pale yellow crystalline powder which, when recrystallised from xylene and dissolved in dimethylformamide, displays a strongly blue fluorescence.

Diethyl 4-formyl-benzenephosphonate was prepared in a known manner by bromination of diethyl 4-methyl-benzenephosphonate and subsequent reaction of the product with hexamethylenetetramine in acetic acid.

EXAMPLE 11

Analogously to Example 4, the compound of the formula

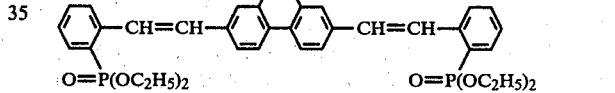

(33)

is obtained from 2,7-di-2-bromostyryl)-9,10-dihydrophenanthrene and triethyl phosphite; when recrystallised from xylene with the addition of bleaching earth and dissolved in dimethylformamide, this compound displays a strongly blue fluorescence.

(32)

The distyryl compounds of the general formula

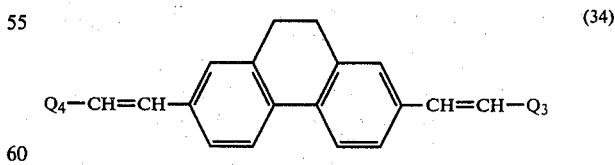

(34)

listed in Table II which follows are also obtained in a similar manner.

TABLE II

| No. | $Q_3$ | $Q_4$ | Colour of the fluorescence in DMF |
|---|---|---|---|
| 35 | 2-phosphonophenyl | 2-phosphonophenyl | reddish-tinged blue |

TABLE II-continued

| No. | $Q_3$ | $Q_4$ | Colour of the fluorescence in DMF |
|---|---|---|---|
| 36 | 3-dipropoxyphosphonophenyl | 3-dipropoxyphosphonophenyl | blue-violet |
| 37 | 2-chlorophenyl | 4-phenylethoxyphosphonylphenyl | blue |
| 38 | phenyl | 4-phenylmethylphosphinylphenyl | blue |

We claim:

1. Distyryl compounds of the formula (II)

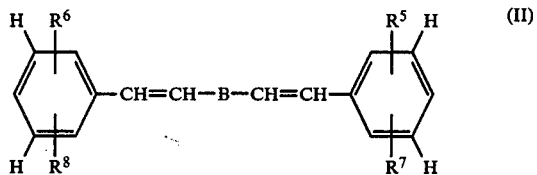 (II)

wherein

B denotes 1,4-phenylene, 4,4'-biphenylene, 1,4- and 2,6-naphthylene, 9,10-dihydro-2,7-phenanthrenylene or 2,7-dibenzofuranylene, $R^5$ denotes a radical of the formula

$R^6$ denotes hydrogen, chlorine, $C_1$-$C_4$-alkyl, sulpho, carboxyl, $C_1$-$C_4$-alkoxy, $C_1$-$C_4$-alkoxycarbonyl, cyano or a radical of the formula

$R^7$ and $R^8$ denote hydrogen, chlorine, $C_1$-$C_4$-alkyl, phenyl which is optionally substituted by methyl, methoxy or chlorine, $C_1$-$C_4$-alkoxy, $C_1$-$C_4$-alkoxycarbonl, cyano, $C_1$-$C_4$-alkylsulphonyl, $C_1$-$C_4$-alkylcarbonyl, hydroxyl or carboxyl, $R^9$ and $R^{10}$ denote $C_1$-$C_4$-alkyl, benzyl, phenyl which is optionally substituted by methyl, methoxy or chlorine or a group of the formula $(OCH_2CH_2)_n$-$OR^{11}$ wherein $R^{11}$ is hydrogen, $C_1$-$C_4$-alkyl, benzyl or phenyl and n is 0 to 7, it being possible for the phosphonic acid group also to be in the form of a salt.

2. Distyryl compounds according to claim 1, of the formula (III)

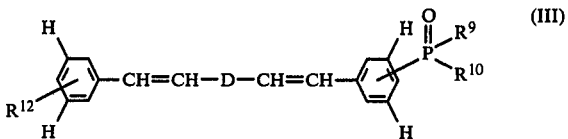 (III)

wherein

D denotes 1,4-phenylene, 4,4'-biphenylylene or 9,10-dihydro—2,7-phenanthrenylene and $R^{12}$ denotes hydrogen, chlorine, $C_1$-$C_4$-alkyl, phenyl, $C_1$-$C_4$-alkoxy, $C_1$-$C_4$-alkoxycarbonyl, cyano, $C_1$-$C_4$alkylcarbonyl, hydroxyl or carboxyl or a radical of the formula

in which $R^9$ and $R^{10}$ have the meaning given in claim 2.

3. A distyryl compound according to claim 1 wherein B denotes 1,4-phenylene or 4,4'-biphenylene.

* * * * *